United States Patent
Möckel et al.

(10) Patent No.: US 6,972,190 B2
(45) Date of Patent: Dec. 6, 2005

(54) NUCLEOTIDE SEQUENCES WHICH CODE FOR THE CSTA GENE

(75) Inventors: Bettina Möckel, Düsseldorf (DE); Achim Marx, Bielefeld (DE); Walter Pfefferle, Halle (DE); Mike Farwick, Bielefeld (DE); Thomas Hermann, Bielefeld (DE)

(73) Assignee: Degussa AG, Düsseldorf (DE)

( * ) Notice: Subject to any disclaimer, the term of this patent is extended or adjusted under 35 U.S.C. 154(b) by 410 days.

(21) Appl. No.: 09/935,799

(22) Filed: Aug. 24, 2001

(65) Prior Publication Data

US 2002/0137912 A1 Sep. 26, 2002

(30) Foreign Application Priority Data

Aug. 26, 2000  (DE) .......................................... 100 42 051

(51) Int. Cl.[7] .................................................. C12P 13/04
(52) U.S. Cl. ..................... 435/106; 435/115; 435/320.1; 435/252.3; 435/252.32; 536/23.1
(58) Field of Search ............................. 536/23.1, 23.2, 536/23.7, 24.3, 24.33; 435/252.32, 320.1, 252.3, 106, 115, 252.1

(56) References Cited

U.S. PATENT DOCUMENTS 6,822,084 B1 * 11/2004 Pompejus et al. ......... 536/23.7
2002/0197605 A1 * 12/2002 Nakagawa et al. ............ 435/6

FOREIGN PATENT DOCUMENTS

| EP | 1 108 790 A2 | 6/2001 |
| WO | WO 99/18228 | 4/1999 |
| WO | WO 01/00804 A2 | 1/2001 |

OTHER PUBLICATIONS

Cole et al. Deciphering the biology of *Mycobacterium tuberculosis* from the complete genome sequence. Nature (1998) 393:537–544.*
Dubey et al. CsrA regulates translation of the *Escherichia coli* carbon starvation gene, cstA, by blocking ribosome access to the cstA transcript. J. Bacteriol. (2003) 185(15):4450–4460.*
GenBank Accession No. BX927149. *Corynebacterium glutamicum* ATCC 13032, IS fingerprint type 4–5, complete genome segment 2/10, Jan. 21, 2004.*
Bernhard J. Eikmanns, et al., "Molecular aspects of lysine, threonine, and isoleucine biosynthesis in *Corynebacterium glutamicum*," Antonie Van Leeuwenhoek, vol. 64, 1993, pp. 145–163.
Nucleotide Sequence ID 4227 and Database EBI, Hinxton, UK; Acession No.: AX124311, May 10, 2001.
Nucleotide Sequence ID 7061 and Database EBI, Hinxton, UK; Acession No.: AX127145, May 10, 2001.
Nucleotide Sequence of Cole, et al. and Database EBI, Hinxton, UK; Acession No.: 283866, Jan. 15, 1997.
GenBank Accession No. P15078, Nov., 1997.

* cited by examiner

*Primary Examiner*—Kathleen Kerr
(74) *Attorney, Agent, or Firm*—Smith, Gambrell & Russell, LLP

(57) ABSTRACT

The invention relates to an isolated polynucleotide from *Corynebacterium glutamicum* having a polynucleotide sequence which codes for the carbon starvation protein A (cstA) gene, and a host-vector system having a coryneform host bacterium in which the cstA gene is present in enhanced form and a vector which carries at least the cstA gene according to SEQ ID NO: 1, and the use of polynucleotides which comprise the sequences according to the invention as hybridization probes.

10 Claims, 2 Drawing Sheets

Figure 1: Plasmid pEC-K18mob2
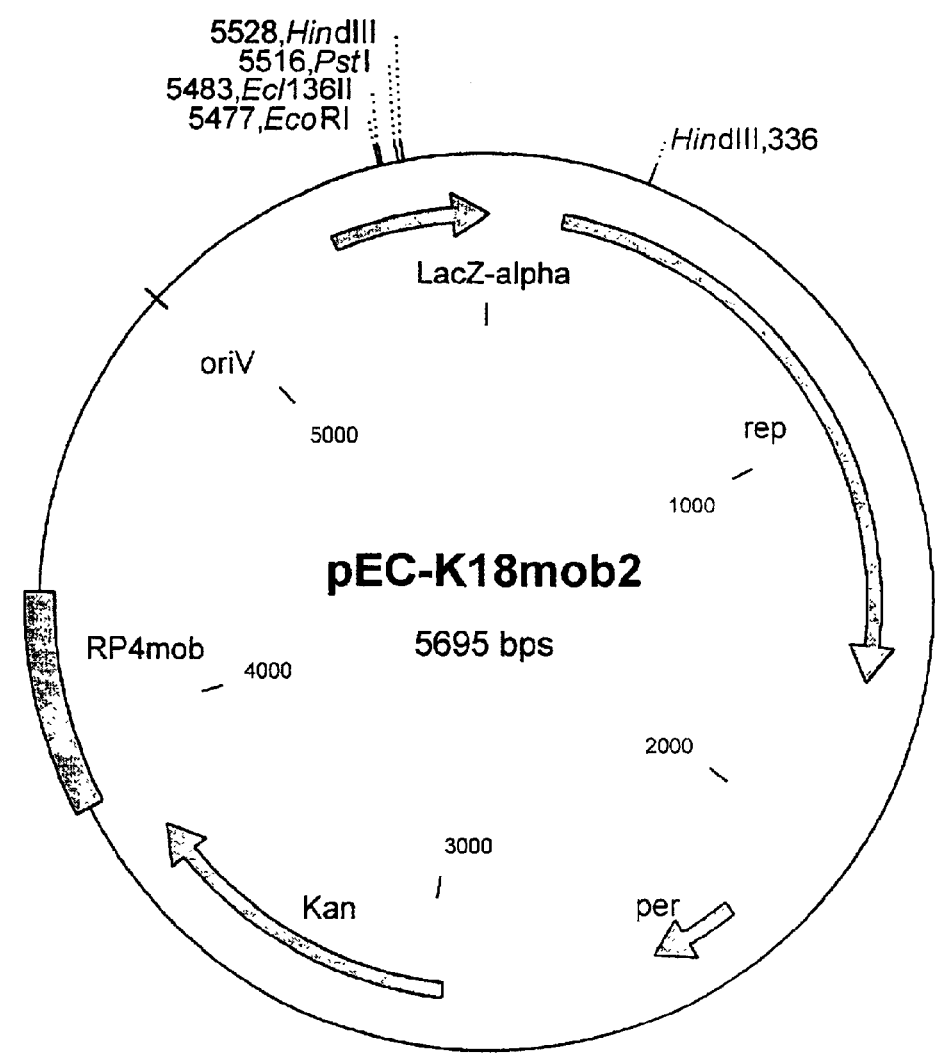

Figure 2: Plasmid pEC-K18mob2cstAexp
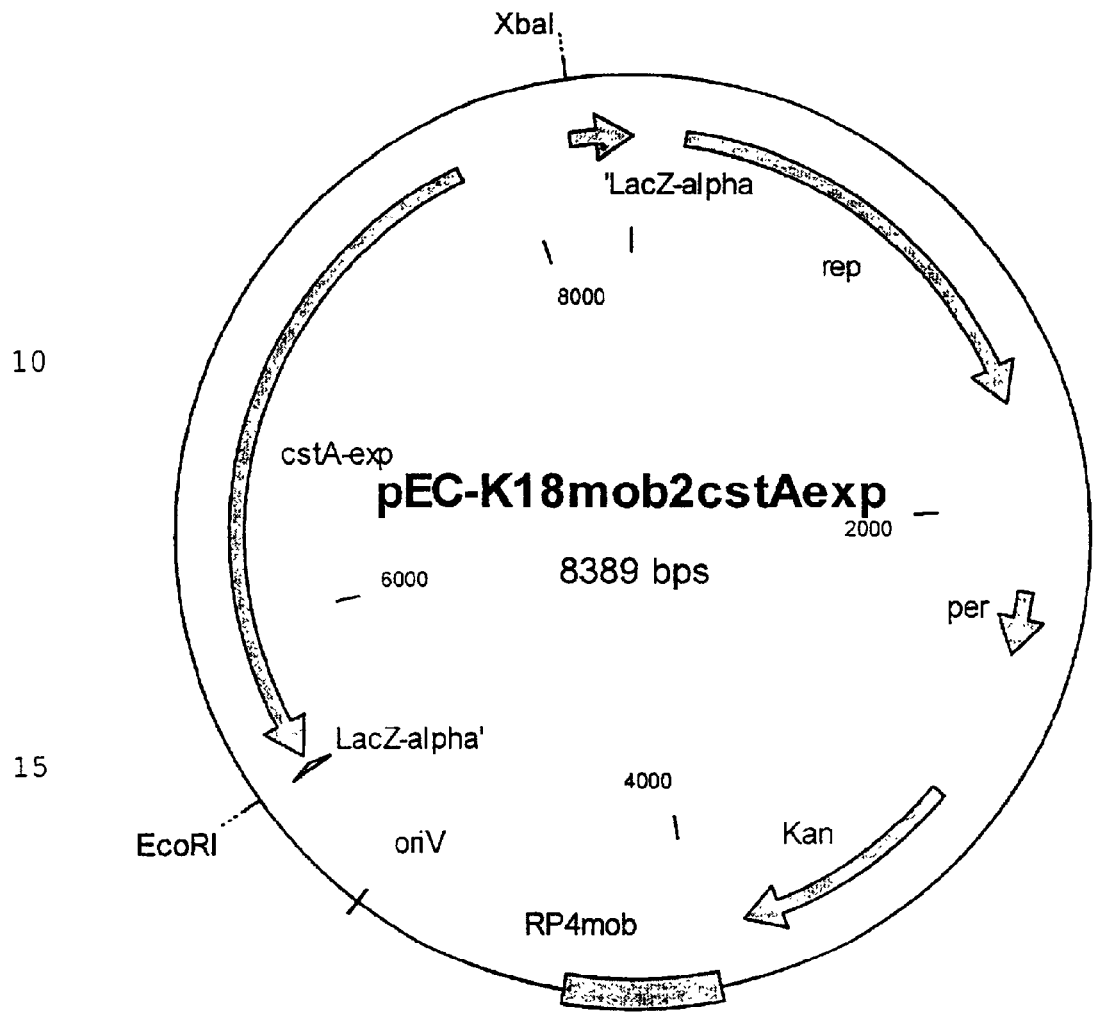

SEQUENCE LISTING

<160> NUMBER OF SEQ ID NOS: 7

<210> SEQ ID NO 1
<211> LENGTH: 2718
<212> TYPE: DNA
<213> ORGANISM: Corynebacterium glutamicum
<220> FEATURE:
<221> NAME/KEY: CDS
<222> LOCATION: (200)..(2515)
<223> OTHER INFORMATION:

<400> SEQUENCE: 1

```
aggatggtat aaatcatctc tcaatgttac ttttccattg ttaagaatta acaactctcg      60
gtgatttgtc gcatacccag ctgtcaaaga tccgatcatc ggcatacaga aacacccatc     120
tggccgaact ttccttttc tgcatgcatt tctgcacaca gtttctgccc gctgtttctg     180
cccgctgttt ctacgcata gtg gct ttg aaa cga ccc gaa gag aaa aca gta     232
                       Met Ala Leu Lys Arg Pro Glu Glu Lys Thr Val
                         1               5                  10 aag atc gtg acc ata aaa cag act gac aac atc aat gac gat gat ttg     280
Lys Ile Val Thr Ile Lys Gln Thr Asp Asn Ile Asn Asp Asp Asp Leu
             15                  20                  25 gtg tac agc aac gct act gac ctt cca gta ggc gtg aag aag tcc cct     328
Val Tyr Ser Asn Ala Thr Asp Leu Pro Val Gly Val Lys Lys Ser Pro
         30                  35                  40 aaa atg tca ccg acc gcc cgc gtt ggt ctc ctt gtc ttt ggg gtt atc     376
Lys Met Ser Pro Thr Ala Arg Val Gly Leu Leu Val Phe Gly Val Ile
     45                  50                  55
```

-continued

| | |
|---|---|
| gcg gcg gtg ggt tgg gga gca atc gct ttc tcc cgt ggc gaa aca atc<br>Ala Ala Val Gly Trp Gly Ala Ile Ala Phe Ser Arg Gly Glu Thr Ile<br>60                        65                        70                        75 | 424 |
| aac tct gtg tgg ctg gtt ttg gcg gca gtt ggt tcc tat atc att gcg<br>Asn Ser Val Trp Leu Val Leu Ala Ala Val Gly Ser Tyr Ile Ile Ala<br>                80                        85                        90 | 472 |
| ttt tct ttc tat gcc cga ctg att gaa tac aaa gtt gtt aag ccg aaa<br>Phe Ser Phe Tyr Ala Arg Leu Ile Glu Tyr Lys Val Val Lys Pro Lys<br>                95                       100                   105 | 520 |
| gat cag cga gca acc ccg gcg gaa tac gtt aat gac ggc aag gac tat<br>Asp Gln Arg Ala Thr Pro Ala Glu Tyr Val Asn Asp Gly Lys Asp Tyr<br>         110                       115                   120 | 568 |
| gtc cca acg gat cgt cgt gtg ctt ttt ggc cac cac ttt gca gct att<br>Val Pro Thr Asp Arg Arg Val Leu Phe Gly His His Phe Ala Ala Ile<br>125                       130                       135 | 616 |
| gca ggt gcc ggt cca ttg gtt gga cct gtc atg gcc gcg cag atg ggc<br>Ala Gly Ala Gly Pro Leu Val Gly Pro Val Met Ala Ala Gln Met Gly<br>140                       145                       150                   155 | 664 |
| tac ctg cca ggc acc ttg tgg att atc ctc ggt gtg att ttc gcc ggt<br>Tyr Leu Pro Gly Thr Leu Trp Ile Ile Leu Gly Val Ile Phe Ala Gly<br>                 160                     165                   170 | 712 |
| gca gtg cag gac tac cta gtg ctg tgg gtg tct act cgt agg cgt gga<br>Ala Val Gln Asp Tyr Leu Val Leu Trp Val Ser Thr Arg Arg Arg Gly<br>               175                    180                   185 | 760 |
| cgc tca ctt ggc cag atg gtt cgt gat gaa atg ggc acg gtc ggt gga<br>Arg Ser Leu Gly Gln Met Val Arg Asp Glu Met Gly Thr Val Gly Gly<br>         190                       195                   200 | 808 |
| gct gcc ggt atc ttg gcg acc atc tcc atc atg atc atc att atc gcg<br>Ala Ala Gly Ile Leu Ala Thr Ile Ser Ile Met Ile Ile Ile Ile Ala<br>205                       210                       215 | 856 |
| gtg ctc gca ttg atc gtg gtt aat gca ctg gct gat tca cca tgg ggc<br>Val Leu Ala Leu Ile Val Val Asn Ala Leu Ala Asp Ser Pro Trp Gly<br>220                       225                       230                   235 | 904 |
| gtt ttc tcc atc acc atg acc atc cca att gca ctg ttc atg ggt gtg<br>Val Phe Ser Ile Thr Met Thr Ile Pro Ile Ala Leu Phe Met Gly Val<br>               240                       245                   250 | 952 |
| tac ttg cgt tac ctg cgc cca ggt cgt gtt act gaa gtg tcc atc atc<br>Tyr Leu Arg Tyr Leu Arg Pro Gly Arg Val Thr Glu Val Ser Ile Ile<br>               255                    260                   265 | 1000 |
| ggt gtg gca ctg ctc ctg ctg gct atc gtt gct ggt ggt tgg gtt gca<br>Gly Val Ala Leu Leu Leu Leu Ala Ile Val Ala Gly Gly Trp Val Ala<br>         270                       275                   280 | 1048 |
| gac acc tca tgg ggc gtg gaa tgg ttc acc tgg tct aag acc act ttg<br>Asp Thr Ser Trp Gly Val Glu Trp Phe Thr Trp Ser Lys Thr Thr Leu<br>285                       290                       295 | 1096 |
| gcg ttg gcc ttg atc ggt tac gga atc atg gct gcg att ttg ccg gtg<br>Ala Leu Ala Leu Ile Gly Tyr Gly Ile Met Ala Ala Ile Leu Pro Val<br>300                       305                       310                   315 | 1144 |
| tgg ctg ctg ctt gca ccg cgc gat tac ctg tct acc ttt atg aag atc<br>Trp Leu Leu Leu Ala Pro Arg Asp Tyr Leu Ser Thr Phe Met Lys Ile<br>               320                       325                   330 | 1192 |
| ggc gtc atc ggt ctg ttg gca gtg ggt att ttg ttc gca cgt cct gag<br>Gly Val Ile Gly Leu Leu Ala Val Gly Ile Leu Phe Ala Arg Pro Glu<br>               335                       340                   345 | 1240 |
| gtg cag atg cct tcc gtg acc tcc ttc gca ctt gag ggc aac ggt ccg<br>Val Gln Met Pro Ser Val Thr Ser Phe Ala Leu Glu Gly Asn Gly Pro<br>         350                       355                   360 | 1288 |
| gtg ttc tct gga agt ctg ttc cca ttc ctg ttc atc acg att gcc tgt<br>Val Phe Ser Gly Ser Leu Phe Pro Phe Leu Phe Ile Thr Ile Ala Cys | 1336 |

-continued

```
            365                 370                 375
ggt gca ctg tct ggt ttc cac gca ctg att tct tca gga acc aca cca      1384
Gly Ala Leu Ser Gly Phe His Ala Leu Ile Ser Ser Gly Thr Thr Pro
380                 385                 390                 395 aag ctt gtg gag aag gaa tcc cag atg cgc atg ctc ggc tac ggc ggc      1432
Lys Leu Val Glu Lys Glu Ser Gln Met Arg Met Leu Gly Tyr Gly Gly
                400                 405                 410 atg ttg atg gaa tct ttc gtg gcg atg atg gca ctg atc acc gct gtt      1480
Met Leu Met Glu Ser Phe Val Ala Met Met Ala Leu Ile Thr Ala Val
            415                 420                 425 att ctg gat cgt cac ctg tac ttc tcc atg aac gct ccg ctg gca ctg      1528
Ile Leu Asp Arg His Leu Tyr Phe Ser Met Asn Ala Pro Leu Ala Leu
        430                 435                 440 act ggt gga gat cca gca acc gca gct gag tgg gtt aac tcc att ggg      1576
Thr Gly Gly Asp Pro Ala Thr Ala Ala Glu Trp Val Asn Ser Ile Gly
    445                 450                 455 ctg aca ggt gcg gat atc acc ccg gaa cag ctg tcg gaa gct gct gaa      1624
Leu Thr Gly Ala Asp Ile Thr Pro Glu Gln Leu Ser Glu Ala Ala Glu
460                 465                 470                 475 agt gtc gga gaa tcc act gtt att tcc cgt acc ggt ggc gca cca acc      1672
Ser Val Gly Glu Ser Thr Val Ile Ser Arg Thr Gly Gly Ala Pro Thr
                480                 485                 490 ttg gcg ttc ggt atg tct gaa atc ctc tcc gga ttc atc ggc ggc gct      1720
Leu Ala Phe Gly Met Ser Glu Ile Leu Ser Gly Phe Ile Gly Gly Ala
            495                 500                 505 gga atg aag gcg ttc tgg tac cac ttc gcc atc atg ttt gag gct ctg      1768
Gly Met Lys Ala Phe Trp Tyr His Phe Ala Ile Met Phe Glu Ala Leu
        510                 515                 520 ttc atc ctc act act gtg gat gca ggt act cgt gtg gct cgc ttt atg      1816
Phe Ile Leu Thr Thr Val Asp Ala Gly Thr Arg Val Ala Arg Phe Met
    525                 530                 535 atg acc gat acc ttg ggc aat gtt cca ggt ctg cgc cgt ttc aag gat      1864
Met Thr Asp Thr Leu Gly Asn Val Pro Gly Leu Arg Arg Phe Lys Asp
540                 545                 550                 555 cct tca tgg act gtc ggt aac tgg att tct acc gtg ttt gtg tgt gct      1912
Pro Ser Trp Thr Val Gly Asn Trp Ile Ser Thr Val Phe Val Cys Ala
                560                 565                 570 cta tgg ggt gct att ttg ctc atg ggt gtt acc gat cca ctg ggc ggc      1960
Leu Trp Gly Ala Ile Leu Leu Met Gly Val Thr Asp Pro Leu Gly Gly
            575                 580                 585 atc aac gtg ctt ttc cca cta ttc ggt atc gct aac cag ctg ctc gcc      2008
Ile Asn Val Leu Phe Pro Leu Phe Gly Ile Ala Asn Gln Leu Leu Ala
        590                 595                 600 gct att gca ctt gct ctc gtg ctg gtt gtt gtg aag aag ggc ctg          2056
Ala Ile Ala Leu Ala Leu Val Leu Val Val Val Lys Lys Gly Leu
    605                 610                 615 tac aag tgg gcg tgg att cca gct gtt cct ttg gca tgg gat ctc att      2104
Tyr Lys Trp Ala Trp Ile Pro Ala Val Pro Leu Ala Trp Asp Leu Ile
620                 625                 630                 635 gtc acg atg act gcg tca tgg cag aag att ttc cac tct gat ccg gct      2152
Val Thr Met Thr Ala Ser Trp Gln Lys Ile Phe His Ser Asp Pro Ala
                640                 645                 650 att ggc tac tgg gct cag aac gcg aac ttc cgc gat gca aag tct caa     2200
Ile Gly Tyr Trp Ala Gln Asn Ala Asn Phe Arg Asp Ala Lys Ser Gln
            655                 660                 665 ggc ctt acc gaa ttt ggt gcc gct aaa tct cct gag gca atc gat gcg     2248
Gly Leu Thr Glu Phe Gly Ala Ala Lys Ser Pro Glu Ala Ile Asp Ala
        670                 675                 680 gtt atc cga aac acc atg att cag ggc atc ttg tcc atc ctg ttc gcg     2296
```

-continued

```
Val Ile Arg Asn Thr Met Ile Gln Gly Ile Leu Ser Ile Leu Phe Ala
            685                 690                 695 gtg ctc gtc ctc gtt gtt gtc ggc gca gcc att gcg gtg tgc atc aag    2344
Val Leu Val Leu Val Val Val Gly Ala Ala Ile Ala Val Cys Ile Lys
700                 705                 710                 715 tcc atc agg gct cgt gca gcc gga aca cct ttg gag acc act gaa gag    2392
Ser Ile Arg Ala Arg Ala Ala Gly Thr Pro Leu Glu Thr Thr Glu Glu
                720                 725                 730 cct gat act gaa tct gag ttc ttc gcc cca act gga ttc ctt gca tct    2440
Pro Asp Thr Glu Ser Glu Phe Phe Ala Pro Thr Gly Phe Leu Ala Ser
            735                 740                 745 tcc agg gat aag gaa gtc cag gcc atg tgg gac gag cgc tac cca ggc    2488
Ser Arg Asp Lys Glu Val Gln Ala Met Trp Asp Glu Arg Tyr Pro Gly
        750                 755                 760 ggt gcg ccc gtg tct tct gga ggg cac taaaacatga tggctcttac          2535
Gly Ala Pro Val Ser Ser Gly Gly His
765                 770 tcatgcactg tggaaaatcc cgcgggcggt gtggtggtat ctcactgagc tcatggggga    2595
cacggcgtat tccaagtatg tggtgcactt aaagcaccac catccggatg ctccgattcc    2655
tactgagcgg gagtattggc gggcaaagta tgcagatcag gacgctaatc ctggtgcccg    2715
ctg                                                                  2718

<210> SEQ ID NO 2
<211> LENGTH: 772
<212> TYPE: PRT
<213> ORGANISM: Corynebacterium glutamicum

<400> SEQUENCE: 2

Met Ala Leu Lys Arg Pro Glu Glu Lys Thr Val Lys Ile Val Thr Ile
1               5                   10                  15

Lys Gln Thr Asp Asn Ile Asn Asp Asp Leu Val Tyr Ser Asn Ala
            20                  25                  30

Thr Asp Leu Pro Val Gly Val Lys Lys Ser Pro Lys Met Ser Pro Thr
        35                  40                  45

Ala Arg Val Gly Leu Leu Val Phe Gly Val Ile Ala Ala Val Gly Trp
    50                  55                  60

Gly Ala Ile Ala Phe Ser Arg Gly Glu Thr Ile Asn Ser Val Trp Leu
65                  70                  75                  80

Val Leu Ala Ala Val Gly Ser Tyr Ile Ile Ala Phe Ser Phe Tyr Ala
                85                  90                  95

Arg Leu Ile Glu Tyr Lys Val Val Lys Pro Lys Asp Gln Arg Ala Thr
            100                 105                 110

Pro Ala Glu Tyr Val Asn Asp Gly Lys Asp Tyr Val Pro Thr Asp Arg
        115                 120                 125

Arg Val Leu Phe Gly His His Phe Ala Ala Ile Ala Gly Ala Gly Pro
    130                 135                 140

Leu Val Gly Pro Val Met Ala Ala Gln Met Gly Tyr Leu Pro Gly Thr
145                 150                 155                 160

Leu Trp Ile Ile Leu Gly Val Ile Phe Ala Gly Ala Val Gln Asp Tyr
                165                 170                 175

Leu Val Leu Trp Val Ser Thr Arg Arg Gly Arg Ser Leu Gly Gln
            180                 185                 190

Met Val Arg Asp Glu Met Gly Thr Val Gly Gly Ala Ala Gly Ile Leu
        195                 200                 205

Ala Thr Ile Ser Ile Met Ile Ile Ile Ile Ala Val Leu Ala Leu Ile
```

-continued

```
                210                 215                 220
Val Val Asn Ala Leu Ala Asp Ser Pro Trp Gly Val Phe Ser Ile Thr
225                 230                 235                 240

Met Thr Ile Pro Ile Ala Leu Phe Met Gly Val Tyr Leu Arg Tyr Leu
                245                 250                 255

Arg Pro Gly Arg Val Thr Glu Val Ser Ile Ile Gly Val Ala Leu Leu
                260                 265                 270

Leu Leu Ala Ile Val Ala Gly Gly Trp Val Ala Asp Thr Ser Trp Gly
                275                 280                 285

Val Glu Trp Phe Thr Trp Ser Lys Thr Thr Leu Ala Leu Ala Leu Ile
                290                 295                 300

Gly Tyr Gly Ile Met Ala Ala Ile Leu Pro Val Trp Leu Leu Leu Ala
305                 310                 315                 320

Pro Arg Asp Tyr Leu Ser Thr Phe Met Lys Ile Gly Val Ile Gly Leu
                325                 330                 335

Leu Ala Val Gly Ile Leu Phe Ala Arg Pro Glu Val Gln Met Pro Ser
                340                 345                 350

Val Thr Ser Phe Ala Leu Glu Gly Asn Gly Pro Val Phe Ser Gly Ser
                355                 360                 365

Leu Phe Pro Phe Leu Phe Ile Thr Ile Ala Cys Gly Ala Leu Ser Gly
                370                 375                 380

Phe His Ala Leu Ile Ser Ser Gly Thr Thr Pro Lys Leu Val Glu Lys
385                 390                 395                 400

Glu Ser Gln Met Arg Met Leu Gly Tyr Gly Met Leu Met Glu Ser
                405                 410                 415

Phe Val Ala Met Met Ala Leu Ile Thr Ala Val Ile Leu Asp Arg His
                420                 425                 430

Leu Tyr Phe Ser Met Asn Ala Pro Leu Ala Leu Thr Gly Gly Asp Pro
                435                 440                 445

Ala Thr Ala Ala Glu Trp Val Asn Ser Ile Gly Leu Thr Gly Ala Asp
                450                 455                 460

Ile Thr Pro Glu Gln Leu Ser Glu Ala Ala Glu Ser Val Gly Glu Ser
465                 470                 475                 480

Thr Val Ile Ser Arg Thr Gly Gly Ala Pro Thr Leu Ala Phe Gly Met
                485                 490                 495

Ser Glu Ile Leu Ser Gly Phe Ile Gly Gly Ala Gly Met Lys Ala Phe
                500                 505                 510

Trp Tyr His Phe Ala Ile Met Phe Glu Ala Leu Phe Ile Leu Thr Thr
                515                 520                 525

Val Asp Ala Gly Thr Arg Val Ala Arg Phe Met Met Thr Asp Thr Leu
                530                 535                 540

Gly Asn Val Pro Gly Leu Arg Arg Phe Lys Asp Pro Ser Trp Thr Val
545                 550                 555                 560

Gly Asn Trp Ile Ser Thr Val Phe Val Cys Ala Leu Trp Gly Ala Ile
                565                 570                 575

Leu Leu Met Gly Val Thr Asp Pro Leu Gly Gly Ile Asn Val Leu Phe
                580                 585                 590

Pro Leu Phe Gly Ile Ala Asn Gln Leu Leu Ala Ala Ile Ala Leu Ala
                595                 600                 605

Leu Val Leu Val Val Val Lys Gly Leu Tyr Lys Trp Ala Trp
                610                 615                 620

Ile Pro Ala Val Pro Leu Ala Trp Asp Leu Ile Val Thr Met Thr Ala
625                 630                 635                 640
```

-continued

```
Ser Trp Gln Lys Ile Phe His Ser Asp Pro Ala Ile Gly Tyr Trp Ala
                645                 650                 655

Gln Asn Ala Asn Phe Arg Asp Ala Lys Ser Gln Gly Leu Thr Glu Phe
            660                 665                 670

Gly Ala Ala Lys Ser Pro Glu Ala Ile Asp Ala Val Ile Arg Asn Thr
        675                 680                 685

Met Ile Gln Gly Ile Leu Ser Ile Leu Phe Ala Val Leu Val Leu Val
    690                 695                 700

Val Val Gly Ala Ala Ile Ala Val Cys Ile Lys Ser Ile Arg Ala Arg
705                 710                 715                 720

Ala Ala Gly Thr Pro Leu Glu Thr Thr Glu Glu Pro Asp Thr Glu Ser
                725                 730                 735

Glu Phe Phe Ala Pro Thr Gly Phe Leu Ala Ser Ser Arg Asp Lys Glu
            740                 745                 750

Val Gln Ala Met Trp Asp Glu Arg Tyr Pro Gly Gly Ala Pro Val Ser
        755                 760                 765

Ser Gly Gly His
    770

<210> SEQ ID NO 3
<211> LENGTH: 149
<212> TYPE: DNA
<213> ORGANISM: Corynebacterium glutamicum

<400> SEQUENCE: 3
caccctactg aacagcttgg tctattgcaa tagactgtgt ggtataaatt tattctcggg      60 taatttctt gacttttccc aactgatttg aaatcgattg cgtacagcta gggttatggg     120
ggtatgacta gccccactct aaatggtgt                                      149

<210> SEQ ID NO 4
<211> LENGTH: 2867
<212> TYPE: DNA
<213> ORGANISM: Corynebacterium glutamicum
<220> FEATURE:
<221> NAME/KEY: CDS
<222> LOCATION: (349)..(2664)
<223> OTHER INFORMATION:

<400> SEQUENCE: 4
caccctactg aacagcttgg tctattgcaa tagactgtgt ggtataaatt tattctcggg      60 taatttctt gacttttccc aactgatttg aaatcgattg cgtacagcta gggttatggg     120
ggtatgacta gccccactct aaatggtgta ggatggtata aatcatctct caatgttact    180
tttccattgt taagaattaa caactctcgg tgatttgtcg catacccagc tgtcaaagat    240
ccgatcatcg gcatacagaa acacccatct ggccgaactt tccttttct gcatgcattt    300 ctgcacacag tttctgcccg ctgtttctgc ccgctgtttc tacgcata gtg gct ttg     357
                                                    Met Ala Leu
                                                      1 aaa cga ccc gaa gag aaa aca gta aag atc gtg acc ata aaa cag act     405
Lys Arg Pro Glu Glu Lys Thr Val Lys Ile Val Thr Ile Lys Gln Thr
  5                  10                  15 gac aac atc aat gac gat gat ttg gtg tac agc aac gct act gac ctt     453
Asp Asn Ile Asn Asp Asp Asp Leu Val Tyr Ser Asn Ala Thr Asp Leu
 20                  25                  30                  35 cca gta ggc gtg aag aag tcc cct aaa atg tca ccg acc gcc cgc gtt     501
Pro Val Gly Val Lys Lys Ser Pro Lys Met Ser Pro Thr Ala Arg Val
             40                  45                  50
```

-continued

```
ggt ctc ctt gtc ttt ggg gtt atc gcg gcg gtg ggt tgg gga gca atc      549
Gly Leu Leu Val Phe Gly Val Ile Ala Ala Val Gly Trp Gly Ala Ile
            55                  60                  65 gct ttc tcc cgt ggc gaa aca atc aac tct gtg tgg ctg gtt ttg gcg      597
Ala Phe Ser Arg Gly Glu Thr Ile Asn Ser Val Trp Leu Val Leu Ala
        70                  75                  80 gca gtt ggt tcc tat atc att gcg ttt tct ttc tat gcc cga ctg att      645
Ala Val Gly Ser Tyr Ile Ile Ala Phe Ser Phe Tyr Ala Arg Leu Ile
    85                  90                  95 gaa tac aaa gtt gtt aag ccg aaa gat cag cga gca acc ccg gcg gaa      693
Glu Tyr Lys Val Val Lys Pro Lys Asp Gln Arg Ala Thr Pro Ala Glu
100                 105                 110                 115 tac gtt aat gac ggc aag gac tat gtc cca acg gat cgt cgt gtg ctt      741
Tyr Val Asn Asp Gly Lys Asp Tyr Val Pro Thr Asp Arg Arg Val Leu
                120                 125                 130 ttt ggc cac cac ttt gca gct att gca ggt gcc ggt cca ttg gtt gga      789
Phe Gly His His Phe Ala Ala Ile Ala Gly Ala Gly Pro Leu Val Gly
            135                 140                 145 cct gtc atg gcc gcg cag atg ggc tac ctg cca ggc acc ttg tgg att      837
Pro Val Met Ala Ala Gln Met Gly Tyr Leu Pro Gly Thr Leu Trp Ile
        150                 155                 160 atc ctc ggt gtg att ttc gcc ggt gca gtg cag gac tac cta gtg ctg      885
Ile Leu Gly Val Ile Phe Ala Gly Ala Val Gln Asp Tyr Leu Val Leu
    165                 170                 175 tgg gtg tct act cgt agg cgt gga cgc tca ctt ggc cag atg gtt cgt      933
Trp Val Ser Thr Arg Arg Arg Gly Arg Ser Leu Gly Gln Met Val Arg
180                 185                 190                 195 gat gaa atg ggc acg gtc ggt gga gct gcc ggt atc ttg gcg acc atc      981
Asp Glu Met Gly Thr Val Gly Gly Ala Ala Gly Ile Leu Ala Thr Ile
                200                 205                 210 tcc atc atg atc atc att atc gcg gtg ctc gca ttg atc gtg gtt aat     1029
Ser Ile Met Ile Ile Ile Ile Ala Val Leu Ala Leu Ile Val Val Asn
            215                 220                 225 gca ctg gct gat tca cca tgg ggc gtt ttc tcc atc acc atg acc atc     1077
Ala Leu Ala Asp Ser Pro Trp Gly Val Phe Ser Ile Thr Met Thr Ile
        230                 235                 240 cca att gca ctg ttc atg ggt gtg tac ttg cgt tac ctg cgc cca ggt     1125
Pro Ile Ala Leu Phe Met Gly Val Tyr Leu Arg Tyr Leu Arg Pro Gly
    245                 250                 255 cgt gtt act gaa gtg tcc atc atc ggt gtg gca ctg ctc ctg ctg gct     1173
Arg Val Thr Glu Val Ser Ile Ile Gly Val Ala Leu Leu Leu Leu Ala
260                 265                 270                 275 atc gtt gct ggt ggt tgg gtt gca gac acc tca tgg ggc gtg gaa tgg     1221
Ile Val Ala Gly Gly Trp Val Ala Asp Thr Ser Trp Gly Val Glu Trp
                280                 285                 290 ttc acc tgg tct aag acc act ttg gcg ttg gcc ttg atc ggt tac gga     1269
Phe Thr Trp Ser Lys Thr Thr Leu Ala Leu Ala Leu Ile Gly Tyr Gly
            295                 300                 305 atc atg gct gcg att ttg ccg gtg tgg ctg ctg ctt gca ccg cgc gat     1317
Ile Met Ala Ala Ile Leu Pro Val Trp Leu Leu Leu Ala Pro Arg Asp
        310                 315                 320 tac ctg tct acc ttt atg aag atc ggc gtc atc ggt ctg ttg gca gtg     1365
Tyr Leu Ser Thr Phe Met Lys Ile Gly Val Ile Gly Leu Leu Ala Val
    325                 330                 335 ggt att ttg ttc gca cgt cct gag gtg cag atg cct tcc gtg acc tcc     1413
Gly Ile Leu Phe Ala Arg Pro Glu Val Gln Met Pro Ser Val Thr Ser
340                 345                 350                 355 ttc gca ctt gag ggc aac ggt ccg gtg ttc tct gga agt ctg ttc cca     1461
Phe Ala Leu Glu Gly Asn Gly Pro Val Phe Ser Gly Ser Leu Phe Pro
```

-continued

```
                360                 365                 370
ttc ctg ttc atc acg att gcc tgt ggt gca ctg tct ggt ttc cac gca    1509
Phe Leu Phe Ile Thr Ile Ala Cys Gly Ala Leu Ser Gly Phe His Ala
            375                 380                 385 ctg att tct tca gga acc aca cca aag ctt gtg gag aag gaa tcc cag    1557
Leu Ile Ser Ser Gly Thr Thr Pro Lys Leu Val Glu Lys Glu Ser Gln
            390                 395                 400 atg cgc atg ctc ggc tac ggc ggc atg ttg atg gaa tct ttc gtg gcg    1605
Met Arg Met Leu Gly Tyr Gly Gly Met Leu Met Glu Ser Phe Val Ala
            405                 410                 415 atg atg gca ctg atc acc gct gtt att ctg gat cgt cac ctg tac ttc    1653
Met Met Ala Leu Ile Thr Ala Val Ile Leu Asp Arg His Leu Tyr Phe
420                 425                 430                 435 tcc atg aac gct ccg ctg gca ctg act ggt gga gat cca gca acc gca    1701
Ser Met Asn Ala Pro Leu Ala Leu Thr Gly Gly Asp Pro Ala Thr Ala
                440                 445                 450 gct gag tgg gtt aac tcc att ggg ctg aca ggt gcg gat atc acc ccg    1749
Ala Glu Trp Val Asn Ser Ile Gly Leu Thr Gly Ala Asp Ile Thr Pro
                455                 460                 465 gaa cag ctg tcg gaa gct gct gaa agt gtc gga gaa tcc act gtt att    1797
Glu Gln Leu Ser Glu Ala Ala Glu Ser Val Gly Glu Ser Thr Val Ile
            470                 475                 480 tcc cgt acc ggt ggc gca cca acc ttg gcg ttc ggt atg tct gaa atc    1845
Ser Arg Thr Gly Gly Ala Pro Thr Leu Ala Phe Gly Met Ser Glu Ile
485                 490                 495 ctc tcc gga ttc atc ggc ggc gct gga atg aag gcg ttc tgg tac cac    1893
Leu Ser Gly Phe Ile Gly Gly Ala Gly Met Lys Ala Phe Trp Tyr His
500                 505                 510                 515 ttc gcc atc atg ttt gag gct ctg ttc atc ctc act act gtg gat gca    1941
Phe Ala Ile Met Phe Glu Ala Leu Phe Ile Leu Thr Thr Val Asp Ala
                520                 525                 530 ggt act cgt gtg gct cgc ttt atg atg acc gat acc ttg ggc aat gtt    1989
Gly Thr Arg Val Ala Arg Phe Met Met Thr Asp Thr Leu Gly Asn Val
                535                 540                 545 cca ggt ctg cgc cgt ttc aag gat cct tca tgg act gtc ggt aac tgg    2037
Pro Gly Leu Arg Arg Phe Lys Asp Pro Ser Trp Thr Val Gly Asn Trp
            550                 555                 560 att tct acc gtg ttt gtg tgt gct cta tgg ggt gct att ttg ctc atg    2085
Ile Ser Thr Val Phe Val Cys Ala Leu Trp Gly Ala Ile Leu Leu Met
565                 570                 575 ggt gtt acc gat cca ctg ggc ggc atc aac gtg ctt ttc cca cta ttc    2133
Gly Val Thr Asp Pro Leu Gly Gly Ile Asn Val Leu Phe Pro Leu Phe
580                 585                 590                 595 ggt atc gct aac cag ctc ctc gcc gct att gca ctt gct ctc gtg ctg    2181
Gly Ile Ala Asn Gln Leu Leu Ala Ala Ile Ala Leu Ala Leu Val Leu
                600                 605                 610 gtt gtt gtg aag aag ggc ctg tac aag tgg gcg tgg att cca gct         2229
Val Val Val Lys Lys Gly Leu Tyr Lys Trp Ala Trp Ile Pro Ala
                615                 620                 625 gtt cct ttg gca tgg gat ctc att gtc acg atg act gcg tca tgg cag    2277
Val Pro Leu Ala Trp Asp Leu Ile Val Thr Met Thr Ala Ser Trp Gln
                630                 635                 640 aag att ttc cac tct gat ccg gct att ggc tac tgg gct cag aac gcg    2325
Lys Ile Phe His Ser Asp Pro Ala Ile Gly Tyr Trp Ala Gln Asn Ala
645                 650                 655 aac ttc cgc gat gca aag tct caa ggc ctt acc gaa ttt ggt gcc gct    2373
Asn Phe Arg Asp Ala Lys Ser Gln Gly Leu Thr Glu Phe Gly Ala Ala
660                 665                 670                 675 aaa tct cct gag gca atc gat gcg gtt atc cga aac acc atg att cag    2421
```

```
Lys Ser Pro Glu Ala Ile Asp Ala Val Ile Arg Asn Thr Met Ile Gln
            680                 685                 690 ggc atc ttg tcc atc ctg ttc gcg gtg ctc gtc ctc gtt gtt gtc ggc      2469
Gly Ile Leu Ser Ile Leu Phe Ala Val Leu Val Leu Val Val Val Gly
            695                 700                 705 gca gcc att gcg gtg tgc atc aag tcc atc agg gct cgt gca gcc gga      2517
Ala Ala Ile Ala Val Cys Ile Lys Ser Ile Arg Ala Arg Ala Ala Gly
            710                 715                 720 aca cct ttg gag acc act gaa gag cct gat act gaa tct gag ttc ttc      2565
Thr Pro Leu Glu Thr Thr Glu Glu Pro Asp Thr Glu Ser Glu Phe Phe
        725                 730                 735 gcc cca act gga ttc ctt gca tct tcc agg gat aag gaa gtc cag gcc      2613
Ala Pro Thr Gly Phe Leu Ala Ser Ser Arg Asp Lys Glu Val Gln Ala
740                 745                 750                 755 atg tgg gac gag cgc tac cca ggc ggt gcg ccc gtg tct tct gga ggg      2661
Met Trp Asp Glu Arg Tyr Pro Gly Gly Ala Pro Val Ser Ser Gly Gly
                760                 765                 770 cac taaaacatga tggctcttac tcatgcactg tggaaaatcc cgcgggcggt           2714
His gtggtggtat ctcactgagc tcatggggga cacggcgtat tccaagtatg tggtgcactt    2774
aaagcaccac catccggatg ctccgattcc tactgagcgg gagtattggc gggcaaagta   2834
tgcagatcag gacgctaatc ctggtgcccg ctg                                 2867

<210> SEQ ID NO 5
<211> LENGTH: 772
<212> TYPE: PRT
<213> ORGANISM: Corynebacterium glutamicum

<400> SEQUENCE: 5

Met Ala Leu Lys Arg Pro Glu Glu Lys Thr Val Lys Ile Val Thr Ile
1               5                   10                  15

Lys Gln Thr Asp Asn Ile Asn Asp Asp Leu Val Tyr Ser Asn Ala
            20                  25                  30

Thr Asp Leu Pro Val Gly Val Lys Lys Ser Pro Lys Met Ser Pro Thr
        35                  40                  45

Ala Arg Val Gly Leu Leu Val Phe Gly Val Ile Ala Ala Val Gly Trp
    50                  55                  60

Gly Ala Ile Ala Phe Ser Arg Gly Glu Thr Ile Asn Ser Val Trp Leu
65                  70                  75                  80

Val Leu Ala Ala Val Gly Ser Tyr Ile Ile Ala Phe Ser Phe Tyr Ala
                85                  90                  95

Arg Leu Ile Glu Tyr Lys Val Val Lys Pro Lys Asp Gln Arg Ala Thr
            100                 105                 110

Pro Ala Glu Tyr Val Asn Asp Gly Lys Asp Tyr Val Pro Thr Asp Arg
        115                 120                 125

Arg Val Leu Phe Gly His His Phe Ala Ile Ala Gly Ala Gly Pro
    130                 135                 140

Leu Val Gly Pro Val Met Ala Ala Gln Met Gly Tyr Leu Pro Gly Thr
145                 150                 155                 160

Leu Trp Ile Ile Leu Gly Val Ile Phe Ala Gly Ala Val Gln Asp Tyr
                165                 170                 175

Leu Val Leu Trp Val Ser Thr Arg Arg Arg Gly Arg Ser Leu Gly Gln
            180                 185                 190

Met Val Arg Asp Glu Met Gly Thr Val Gly Gly Ala Ala Gly Ile Leu
        195                 200                 205
```

-continued

```
Ala Thr Ile Ser Ile Met Ile Ile Ile Ala Val Leu Ala Leu Ile
    210                 215                 220

Val Val Asn Ala Leu Ala Asp Ser Pro Trp Gly Val Phe Ser Ile Thr
225                 230                 235                 240

Met Thr Ile Pro Ile Ala Leu Phe Met Gly Val Tyr Leu Arg Tyr Leu
                245                 250                 255

Arg Pro Gly Arg Val Thr Glu Val Ser Ile Ile Gly Val Ala Leu Leu
                260                 265                 270

Leu Leu Ala Ile Val Ala Gly Gly Trp Val Ala Asp Thr Ser Trp Gly
            275                 280                 285

Val Glu Trp Phe Thr Trp Ser Lys Thr Thr Leu Ala Leu Ala Leu Ile
            290                 295                 300

Gly Tyr Gly Ile Met Ala Ala Ile Leu Pro Val Trp Leu Leu Leu Ala
305                 310                 315                 320

Pro Arg Asp Tyr Leu Ser Thr Phe Met Lys Ile Gly Val Ile Gly Leu
                325                 330                 335

Leu Ala Val Gly Ile Leu Phe Ala Arg Pro Glu Val Gln Met Pro Ser
            340                 345                 350

Val Thr Ser Phe Ala Leu Glu Gly Asn Gly Pro Val Phe Ser Gly Ser
            355                 360                 365

Leu Phe Pro Phe Leu Phe Ile Thr Ile Ala Cys Gly Ala Leu Ser Gly
    370                 375                 380

Phe His Ala Leu Ile Ser Ser Gly Thr Thr Pro Lys Leu Val Glu Lys
385                 390                 395                 400

Glu Ser Gln Met Arg Met Leu Gly Tyr Gly Met Leu Met Glu Ser
                405                 410                 415

Phe Val Ala Met Met Ala Leu Ile Thr Ala Val Ile Leu Asp Arg His
                420                 425                 430

Leu Tyr Phe Ser Met Asn Ala Pro Leu Ala Leu Thr Gly Gly Asp Pro
    435                 440                 445

Ala Thr Ala Ala Glu Trp Val Asn Ser Ile Gly Leu Thr Gly Ala Asp
450                 455                 460

Ile Thr Pro Glu Gln Leu Ser Glu Ala Ala Glu Ser Val Gly Glu Ser
465                 470                 475                 480

Thr Val Ile Ser Arg Thr Gly Gly Ala Pro Thr Leu Ala Phe Gly Met
                485                 490                 495

Ser Glu Ile Leu Ser Gly Phe Ile Gly Gly Ala Gly Met Lys Ala Phe
            500                 505                 510

Trp Tyr His Phe Ala Ile Met Phe Glu Ala Leu Phe Ile Leu Thr Thr
            515                 520                 525

Val Asp Ala Gly Thr Arg Val Ala Arg Phe Met Met Thr Asp Thr Leu
530                 535                 540

Gly Asn Val Pro Gly Leu Arg Arg Phe Lys Asp Pro Ser Trp Thr Val
545                 550                 555                 560

Gly Asn Trp Ile Ser Thr Val Phe Val Cys Ala Leu Trp Gly Ala Ile
                565                 570                 575

Leu Leu Met Gly Val Thr Asp Pro Leu Gly Gly Ile Asn Val Leu Phe
            580                 585                 590

Pro Leu Phe Gly Ile Ala Asn Gln Leu Leu Ala Ala Ile Ala Leu Ala
            595                 600                 605

Leu Val Leu Val Val Val Lys Lys Gly Leu Tyr Lys Trp Ala Trp
    610                 615                 620

Ile Pro Ala Val Pro Leu Ala Trp Asp Leu Ile Val Thr Met Thr Ala
```

-continued

```
                          625                 630                 635                 640

Ser Trp Gln Lys Ile Phe His Ser Asp Pro Ala Ile Gly Tyr Trp Ala
                645                 650                 655

Gln Asn Ala Asn Phe Arg Asp Ala Lys Ser Gln Gly Leu Thr Glu Phe
                660                 665                 670

Gly Ala Ala Lys Ser Pro Glu Ala Ile Asp Ala Val Ile Arg Asn Thr
                675                 680                 685

Met Ile Gln Gly Ile Leu Ser Ile Leu Phe Ala Val Leu Val Leu Val
            690                 695                 700

Val Val Gly Ala Ala Ile Ala Val Cys Ile Lys Ser Ile Arg Ala Arg
705                 710                 715                 720

Ala Ala Gly Thr Pro Leu Glu Thr Thr Glu Glu Pro Asp Thr Glu Ser
                725                 730                 735

Glu Phe Phe Ala Pro Thr Gly Phe Leu Ala Ser Ser Arg Asp Lys Glu
                740                 745                 750

Val Gln Ala Met Trp Asp Glu Arg Tyr Pro Gly Gly Ala Pro Val Ser
                755                 760                 765

Ser Gly Gly His
            770

<210> SEQ ID NO 6
<211> LENGTH: 20
<212> TYPE: DNA
<213> ORGANISM: Corynebacterium glutamicum

<400> SEQUENCE: 6
caccctactg aacagcttgg                                                  20

<210> SEQ ID NO 7
<211> LENGTH: 20
<212> TYPE: DNA
<213> ORGANISM: Corynebacterium glutamicum

<400> SEQUENCE: 7
cagtgcatga gtaagagcca                                                  20
```

NUCLEOTIDE SEQUENCES WHICH CODE FOR THE CSTA GENE

BACKGROUND OF THE INVENTION

The invention provides nucleotide sequences from coryneform bacteria which code for the cstA gene and a process for the fermentative preparation of amino acids, in particular L-lysine, using bacteria in which the cstA gene is enhanced. All references cited herein are expressly incorporated by reference. Incorporation by reference is also designated by the term "I.B.R." following any citation.

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

The inventors had the object of providing new measures for improved fermentative preparation of amino acids, in particular L-lysine.

BRIEF SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

When lysine or L-lysine are mentioned in the following, not only the base but also the salts, such as e.g. lysine monohydrochloride or lysine sulfate, are meant by this.

The invention provides an isolated polynucleotide from coryneform bacteria, comprising a polynucleotide sequence which codes for the cstA gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of carbon starvation protein A.

The invention also provides the above-mentioned polynucleotide, this preferably being a DNA which is capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide comprising the nucleotide sequence as shown in SEQ ID No. 1;

a polynucleotide which codes for a polypeptide which comprises the amino acid sequence as shown in SEQ ID No. 2;

a vector containing the polynucleotide according to the invention, in particular a shuttle vector or plasmid vector, and coryneform bacteria serving as the host cell, which contain the vector or in which the cstA gene is enhanced.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

BRIEF DESCRIPTION OF THE FIGURES

FIG. 1 is a map of the plasmid pEC-K18mob2; and

FIG. 2 is a Map of the plasmid pEC-K18mob2cstAexp.

The abbreviations and designations used have the following meaning:

Kan: Resistance gene for kanamycin
cstA-exp: cstA gene from *C. glutamicum*
LacZ-alpha: lacZα gene fragment from *E. coli*
LacZ-alpha: 5'-Terminus of the lacZα gene fragment
LacZ-alpha: 3'-Terminus of the lacZα gene fragment
per: Gene for control of the number of copies from PGA1
oriV: ColE1-similar origin from pMB1
rep: Plasmid-coded replication region from *C. glutamicum* plasmid pGA1
RP4mob: RP4 mobilization site
EcoRI: Cleavage site of the restriction enzyme EcoRI
HindIII: Cleavage site of the restriction enzyme HindIII
Ecl136:II: Cleavage site of the restriction enzyme Ecl136II
XbaI: Cleavage site of the restriction enzyme XbaI

DETAILED DESCRIPTION OF THE INVENTION

Polynucleotide sequences according to the invention are suitable as hybridization probes for RNA, cDNA and DNA, in order to isolate, in the full length, nucleic acids or polynucleotides or genes which code for carbon starvation protein A, or to isolate those nucleic acids or polynucleotides or genes which have a high similarity of sequence with that of the cstA gene. They are also suitable for incorporation into so-called "arrays", "micro arrays" or "DNA chips" in order to detect and determine the corresponding polynucleotides.

Polynucleotide sequences according to the invention are furthermore suitable as primers with the aid of which DNA of genes which code for carbon starvation protein A can be prepared with the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of carbon starvation protein A, and also those which are at least 70% to 80%, preferably at least 81% to 85%, particularly preferably at least 91%, 93%, 95%, 97% or 99% identical to the polypeptide according to SEQ ID No. 2 and have the activity mentioned.

The invention moreover provides a process for the fermentative preparation of amino acids, in particular L-lysine, using coryneform bacteria which in particular already produce amino acids, and in which the nucleotide sequences which code for the cstA gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms which the present invention provides can prepare L-amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine-producing mutants or strains prepared therefrom, such as, for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The inventors have succeeded in isolating the new cstA gene of *C. glutamicum* which codes for carbon starvation protein A.

To isolate the cstA gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164) I.B.R. in the *E. coli* K-12 strain NM554 (Raleigh et al., 1988, Nucleic Acids Research 16:1563–1575 I.B.R.).

Börmann et al. (Molecular Microbiology 6(3), 317–326) (1992)) I.B.R. in turn describe a gene library of *C. glutamicum* ATCC13032 using the cosmid pHC79 (Hohn and Collins, Gene 11, 291–298 (1980)) I.B.R.

To prepare a gene library of *C. glutamicum* in *E. coli* it is also possible to use plasmids such as pBR322 (Bolivar, Life Sciences, 25, 807–818 (1979) I.B.R.) or pUC9 (Vieira et al., 1982, Gene, 19:259–268 I.B.R.). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649) I.B.R. The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977) I.B.R.

The resulting DNA sequences can then be investigated with known algorithms or sequence analysis programs, such as e.g. that of Staden (Nucleic Acids Research 14, 217–232 (1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* which codes for the cstA gene and which, as SEQ ID No. 1, is a constituent of the present invention has been obtained in this manner. The amino acid sequence of the corresponding protein has furthermore been derived from the present DNA sequence by the methods described above. The resulting amino acid sequence of the cstA gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996) I.B.R.

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and subsequently 0.5×SSC (The DIG System User's Guide for Filter Hybridisation, Boehringer Mannheim, Mannheim, Germany, 1995 I.B.R.) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558 I.B.R.).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R.

It has been found that coryneform bacteria produce amino acids, in particular L-lysine, in an improved manner after over-expression of the cstA gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative lysine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in European Patent Specification 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in Patent Application WO 96/15246 I.B.R., in Malumbres et al. (Gene 134, 15–24 (1993)) I.B.R., in Japanese Laid-Open Specification JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

By way of example, for enhancement the cstA gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554 I.B.R.), pEKEx1 (Eikmanns et al., Gene 102:93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as e.g. those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) I.B.R. for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)) I.B.R., pK18mob or pK19mob (Schäfer et al., Gene 145, 69–73 (1994) I.B.R.), pGEM-T (Promega corporation, Madison, Wis., USA), pCR2.1-TOPO (Shuman (1994). Journal of Biological Chemistry 269:32678–84 I.B.R.,; U.S. Pat. No. 5,487,993 I.B.R.), pCR®Blunt (Invitrogen, Groningen, Holland; Bernard et al., Journal of Molecular Biology, 234: 534–541 (1993)) I.B.R., pEM1 (Schrumpf et al, 1991, Journal of Bacteriology 173:4510–4516 I.B.R.) or pBGS8 (Spratt et al., 1986, Gene 41: 337–342 I.B.R.). The plasmid vector which contains the gene to be amplified is then transferred into the desired strain of C. glutamicum by conjugation or transformation. The method of conjugation is described, for example, by Schafer et al. (Applied and Environmental Microbiology 60, 756–759 (1994)) I.B.R. Methods for transformation are described, for example, by Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross over" event, the resulting strain contains at least two copies of the gene in question.

In addition, it may be advantageous for the production of amino acids, in particular L-lysine, to enhance one or more enzymes of the particular biosynthesis pathway, of glycolysis, of anaplerosis, of the citric acid cycle or of amino acid export and optionally regulatory proteins, in addition to the cstA gene.

Thus, for example, for the preparation of amino acids, in particular L-lysine, one or more genes chosen from the group consisting of the dapA gene which codes for dihydrodipicolinate synthase (EP-B 0 197 335 I.B.R.), the gap gene which codes for glyceraldehyde 3-phosphate dehydrogenase (Eikmanns (1992), Journal of Bacteriology 174:6076–6086 I.B.R.), the tpi gene which codes for triose phosphate isomerase (Eikmanns (1992), Journal of Bacteriology 174:6076–6086 I.B.R.), the pgk gene which codes for 3-phosphoglycerate kinase (Eikmanns (1992), Journal of Bacteriology 174:6076–6086 I.B.R.), the pyc gene which codes for pyruvate carboxylase (Peters-Wendisch et al. (Microbiology 144, 915–927 (1998) I.B.R.), the lysC gene which codes for a feed back resistant aspartate kinase (Accession No. P26512; EP-B-0387527 I.B.R.; EP-A-0699759 I.B.R.), the lysE gene which codes for lysine export (DE-A-195 48 222 I.B.R.), the zwa1 gene which codes for the Zwa1 protein (DE: 19959328.0 I.B.R., DSM 13115) can be enhanced, in particular over-expressed.

It may furthermore be advantageous for the production of amino acids, in particular L-lysine, in addition to the enhancement of the cstA gene, for one or more genes chosen from the group consisting of the pck gene which codes for phosphoenol pyruvate carboxykinase (DE 199 50 409.1 I.B.R.; DSM 13047), the pgi gene which codes for glucose 6-phosphate isomerase (U.S. Ser. No. 09/396,478 I.B.R.; DSM 12969), the poxB gene which codes for pyruvate oxidase (DE: 1995 1975.7 I.B.R.; DSM 13114), the zwa2 gene which codes for the Zwa2 protein (DE: 19959327.2 I.B.R. DSM 13113)

to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

In addition to over-expression of the cstA gene it may furthermore be advantageous, for the production of amino acids, in particular L-lysine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982) I.B.R.

The microorganisms prepared according to the invention can be cultured continuously or discontinuously in the batch process (batch culture) or in the fed batch (feed process) or repeated fed batch process (repetitive feed process) for the purpose of production of amino acids, in particular L-lysine. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) I.B.R. or in the textbook by Storhas (Bioreaktoren und periphere Einrichtungen [Bioreactors and Peripheral Equipment] (Vieweg Verlag, Braunschweig/Wiesbaden, 1994)) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus.

The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The analysis of lysine can be carried out by ion exchange chromatography with subsequent ninhydrin derivation, as described by Spackman et al. (Analytical Chemistry, 30, (1958), 1190) I.B.R.

The process according to the invention is used for the fermentative preparation of amino acids, in particular L-lysine.

The following microorganisms have been deposited as pure cultures at the Deutsche Sammlung für Mikroorganismen und Zellkulturen (DSMZ=German Collection of Microorganisms and Cell Cultures, Mascheroder Weg 1b D-38124 Braunschweig, Germany) in accordance with the Budapest Treaty:

C. glutamicum strain DSM 5715/pEC-K18mob2 on 20th Jan. 2000 as DSM 13245,

Escherichia coli DH5alphamcr/pEC-K18mob2cstAexp on 22nd Aug. 2000 as DSM 13671.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA) I.B.R. Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) I.B.R. and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164 I.B.R.), obtained from Stratagene (La Jolla, USA, Product Description Super-Cos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575 I.B.R.) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor I.B.R.), the cells being plated out on LB agar (Lennox, 1955, Virology, 1:190 I.B.R.) with 100 mg/l ampicillin. After incubation overnight at 37° C., recombinant individual clones were selected.

EXAMPLE 2

Isolation and Sequencing of the cstA Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor I.B.R.), the DNA mixture being incubated overnight with T4 ligase (Pharmacia Biotech, Freiburg, Germany). This ligation mixture was then electroporated (Tauch et al. 1994, FEMS Microbiol Letters, 123:343–7 I.B.R.) into the *E. coli* strain DH5αMCR (Grant, 1990, Proceedings of the National Academy of Sciences U.S.A., 87:4645–4649 I.B.R.) and plated out on LB agar (Lennox, 1955, Virology, 1:190 I.B.R.) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467 I.B.R.) with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231 I.B.R.) version 97-0. The individual sequences of the pZerol derivatives were assembled to a continuous contig. The computer-assisted coding region analysis was prepared with the XNIP program (Staden, 1986, Nucleic Acids Research, 14:217–231 I.B.R.).

The resulting nucleotide sequence is shown in SEQ ID No. 1. Analysis of the nucleotide sequence showed an open reading frame of 2316 base pairs, which was called the cstA gene. The cstA gene codes for a protein of 772 amino acids (SEQ ID No.2).

The DNA section lying upstream of SEQ ID No. 1 was identified in the same way, this section being shown in SEQ ID No. 3. The cstA gene region extended by SEQ ID No. 3 is shown in SEQ ID No. 4. SEQ ID NO: 5 shows the amino acid sequence encoded by SEQ ID NO: 4.

EXAMPLE 3

Preparation of a Shuttle Vector pEC-K18mob2cstAexp for enhancement of the cstA Gene in *C. glutamicum*
3.1 Cloning of the cstA Gene From the strain ATCC 13032, chromosomal DNA was isolated by the method of Eikmanns et al. (Microbiology 140:1817–1828 (1994)) I.B.R. On the basis of the sequence of the cstA gene known for *C. glutamicum* from example 2, the following oligonucleotides were chosen for the polymerase chain reaction (see SEQ ID No. 6 and SEQ ID No. 7):

```
cstA-exp1:
5' CAC CCT ACT GAA CAG CTT GG 3'  SEQ ID NO: 6 cstA-exp2:
5' CAG TGC ATG AGT AAG AGC CA 3'  SEQ ID NO: 7
```

The primers shown were synthesized by ARK Scientific GmbH Biosystems (Darmstadt, Germany) and the PCR reaction was carried out by the standard PCR method of Innis et al. (PCR protocols. A guide to methods and applications, 1990, Academic Press) I.B.R. with Pwo-Polymerase from Roche Diagnostics GmbH (Mannheim, Germany). With the aid of the polymerase chain reaction, the primers allow amplification of a DNA fragment approx. 2.7 kb in size, which carries the cstA gene with the potential promoter region. The DNA sequence of the amplified DNA fragment was checked by sequencing.

3.2 Preparation of the *E. coli*—*C. glutamicum* Shuttle Vector pEC-K18mob2

The *E. coli*—*C. glutamicum* shuttle vector was constructed according to the prior art. The vector contains the replication region rep of the plasmid pGA1 including the replication effector per (U.S. Pat. No. 5,175,108 I.B.R.; Nesvera et al., Journal of Bacteriology 179, 1525–1532 (1997)) I.B.R., the kanamycin resistance-imparting aph(3')-IIa gene of the transposon Tn5 (Beck et al., Gene 19, 327–336 (1982) I.B.R.), the replication region oriV of the plasmid pMB1 (Sutcliffe, Cold Spring Harbor Symposium on Quantitative Biology 43, 77–90 (1979) I.B.R.), the lacZα gene fragment including the lac promoter and a multiple cloning site (mcs) (Norrander, J. M. et al., Gene 26, 101–106 (1983) I.B.R.) and the mob region of the plasmid RP4 (Simon et al., Bio/Technology 1:784–791 (1983) I.B.R.). The vector constructed was transformed in the *E. coli* strain DH5α (Hanahan, In: DNA Cloning. A Practical Approach. Vol. I, IRL-Press, Oxford, Washington D.C., USA). Selection for plasmid-carrying cells was made by plating out the transformation batch on LB agar (Sambrook et al., Molecular cloning: A Laboratory Manual, $2^{nd}$ Ed., Cold Spring Harbor Laboratory Press, Cold Spring Harbor, N.Y. I.B.R.), which had been supplemented with 25 mg/l kanamycin. Plasmid DNA was isolated from a transformant with the aid of the QIAprep Spin Miniprep Kit from Qiagen and checked by restriction with the restriction enzymes EcoRI and HindIII with subsequent agarose gel electrophoresis (0.8%). The plasmid was called pEC-K18mob2 and is shown in FIG. 1.

3.3 Cloning of cstA in the *E. coli*—*C. glutamicum* shuttle vector pEC-K18mob2

The *E. coli*-*C. glutamicum* shuttle vector pEC-K18mob2 described in example 3.2 was used as the vector. DNA of this plasmid was cleaved completely with the restriction enzyme Ecl136II and then dephosphorylated with shrimp alkaline phosphatase (Roche Diagnostics GmbH, Mannheim, Germany, Product Description SAP, Product No. 1758250).

The cstA fragment obtained as described in example 3.1 was mixed with the prepared vector pEC-K18mob2 and the batch was treated with T4 DNA ligase (Amersham Pharmacia, Freiburg, Germany, Product Description T4-DNA-Ligase, Code no.27-0870-04). The ligation batch was transformed in the *E. coli* strain DH5αmcr (Grant, 1990, Proceedings of the National Academy of Sciences U.S.A., 87:4645–4649 I.B.R.). Selection of plasmid-carrying cells was made by plating out the transformation batch on LB agar (Lennox, 1955, Virology, 1:190 I.B.R.) with 25 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes EcoRI and XbaI to check the plasmid by subsequent agarose gel electrophoresis. The plasmid obtained was called pEC-K18mob2cstAexp. It is shown in FIG. 2.

EXAMPLE 4

Transformation of the Strain DSM5715 with the Plasmid pEC-K18mob2cstAexp

The strain DSM5715 was transformed with the plasmid pEC-K18mob2cstAexp using the electroporation method described by Liebl et al., (FEMS Microbiology Letters, 53:299–303 (1989)) I.B.R. Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927 I.B.R.), cleaved with the restriction endonucleases EcoRI and XbaI, and the plasmid was checked by subsequent agarose gel electrophoresis. The strain obtained was called DSM5715/pEC-K18mob2cstAexp.

EXAMPLE 5

Preparation of Lysine

The *C. glutamicum* strain DSM5715/pEC-K18mob2cstAexp obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/L) was added to this. The preculture was incubated for 16 hours at 33° C. at 240 rpm on a shaking machine. A main culture was seeded from this preculture such that the initial OD (660 nm) of the main culture was 0.05. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
|---|---|---|
| DSM5715 | 7.6 | 13.5 |
| DSM5715/pEC-K18mob2cstAexp | 12.2 | 16.1 |

This application claims priority to German Priority Document Application No. 100 42 051.6, filed on Aug. 26, 2000. The German Priority Document is hereby incorporated by reference in its entirety.

We claim:

1. An isolated polynucleotide, comprising the nucleic acid sequence as shown in SEQ ID NO: 1.

2. An isolated polynucleotide comprising the complete complement of SEQ ID NO: 1.

3. A vector comprising the isolated polynucleotide of claim 1.

4. The shuttle vector *Escherichia coli* DH5 alphamcr/pEC-K18mob2cstAexp deposited as DSM 13671.

5. A bacterium transformed with the isolated polynucleotide of claim 1.

6. A coryneform bacterium comprising a vector which comprises a polynucleotide according to claim 1.

7. A method for the fermentative prepartion of L-amino acid in coryneform bacteria comprising:
   a) fermenting the coryneform bacteria of claim 6, and
   b) producing said L-amino acid.

8. A method according to claim 7 further comprising:
   c) isolating said L-amino acid.

9. A method according to claim 7, wherein the L-amino acid is lysine.

10. A method according to claim 7, wherein the shuttle vector Escherchia coli DH5alphamcr/pEC-K18mob2cstAexp is used.

* * * * *